United States Patent [19]

Ferland et al.

[11] Patent Number: 5,616,831
[45] Date of Patent: Apr. 1, 1997

[54] PROCESS AND APPARATUS FOR CONTROLLING GRAVITY SETTLING SYSTEM

[75] Inventors: Pierre Ferland, Jonquiere; Leopold Tremblay, Chicoutimi; Jean Doucet, Jonquiere, all of Canada

[73] Assignee: Alcan International Limited, Montreal, Canada

[21] Appl. No.: 426,690

[22] Filed: Apr. 21, 1995

[51] Int. Cl.[6] .................................................. G01N 15/04
[52] U.S. Cl. ...................... 73/61.63; 73/53.01; 73/865.6
[58] Field of Search ............................... 73/61.63, 865.6, 73/53.01

[56] References Cited

U.S. PATENT DOCUMENTS

| | | | |
|---|---|---|---|
| 3,904,521 | 9/1975 | Stopka | 210/44 |
| 4,040,954 | 8/1977 | Chandler | 210/42 |
| 4,076,620 | 2/1978 | Opferkuch et al. | 210/45 |
| 4,273,658 | 6/1981 | Karman | 210/709 |
| 4,318,296 | 3/1982 | Parker et al. | 73/61.4 |
| 4,354,920 | 10/1982 | Rosenthal et al. | 208/10 |
| 4,431,543 | 2/1984 | Matsuo et al. | 210/605 |
| 4,455,220 | 6/1984 | Pasrker et al. | 208/161 |
| 4,493,765 | 1/1985 | Long et al. | 208/309 |
| 4,543,178 | 9/1985 | Goldstein | 209/2 |
| 4,654,418 | 3/1987 | Berger et al. | 528/486 |
| 4,692,311 | 9/1987 | Parker et al. | 422/122 |
| 4,822,482 | 4/1989 | Hollingsworth | 209/158 |
| 5,464,528 | 11/1995 | Owen et al. | 208/161 |

OTHER PUBLICATIONS

Valheim, "Flocculant Optimization Cuts Chemical Costs and Boosts Performance" Process & Control Engineering, Aug. 1990.

Eisenlauer and Horn, (Z. Wasser Abwasser Forsch. 16 (1983) Nr. 1, S. 9–15.

*Primary Examiner*—Hezron E. Williams
*Assistant Examiner*—Jay L. Politzer
*Attorney, Agent, or Firm*—Cooper & Dunham LLP

[57] ABSTRACT

A testing device is described for use in determining optimum operating conditions for a full size industrial continuous gravity settling unit and for the design of such settling unit. The testing device comprises an elongated, cylindrical settling column having concentric, inner and outer transparent cylindrical walls forming an annular space therebetween filled with transparent heat exchange liquid, with the inner wall defining a cylindrical settling cell. A cylindrical feedwell extends downwardly into the top end of the settling cell, an overflow outlet opening is provided in the inner wall at a location above the bottom end of said feedwell, a solids discharge opening is provided at the bottom of the settling cell and a rotating rake is provided at the bottom of the settling cell for compacting collected solids. The device also includes pump means for providing smooth, continuous flows of slurry and flocculant, mixing means for mixing together the slurry and flocculant, and means for measuring and controlling flow rates and temperatures. The testing device is utilized by observing the position and shape of a stream of agglomerated solids leaving the bottom of the feedwell of the settling column and adjusting the flow rate of at least one of the flow rate of the stream of suspended solids and the flow rate of the stream of flocculating agent to the settling column such that the stream of agglomerated solids leaving the feedwell displays hindered settling, and utilizing the adjusted flow rates of the suspended solids stream and the flocculant stream to determine the optimum operating conditions for an industrial settling unit.

21 Claims, 4 Drawing Sheets

PROCESS AND APPARATUS FOR CONTROLLING GRAVITY SETTLING SYSTEM

BACKGROUND OF THE INVENTION

1. Field of the Invention

This invention relates to continuous thickeners, clarifiers and similar gravititational settling devices for separating feed slurries or pulps into clarified liquid and sludge and is particularly concerned with a method and device for controlling the operation or design of such settling devices.

2. Description of the Prior Art

Continuous thickeners, clarifiers and similar gravitational settling devices are widely used in the chemical and metallurgical industries for the removal of liquids from slurries, metallurgical pulps, sewage and other liquid-solid suspensions. Such devices generally include a circular tank having a cylindrical center feedwell which extends downwardly into the vessel and is open at the bottom. The incoming slurry or pulp passes through a feed pipe or launder into the upper part of this central feedwell and is introduced into the surrounding liquid through the bottom of the feedwell in a manner designed to create a minimum of turbulence. This makes it possible to contain the bulk of the solids near the center of the unit. On leaving the feedwell, the liquid entering with the pulp or slurry tends to move outwardly in a radial direction and flow upwardly toward a peripheral overflow launder. The solids suspended in the slurry or pulp settle downwardly through the slow-moving liquid and accumulate on the bottom of the unit. These solids are compacted as they accumulate and are slowly moved toward a bottom sludge discharge opening by means of slowly rotating rakes suspended a short distance above the bottom. The rakes aid in compacting the sludge and reduce its liquid content.

During the normal operation of a thickener, decanter, clarifier or similar continuous gravity settling device of the type referred to above, a series of relatively well-defined, vertically-spaced zones exist within the settler. The uppermost of these zones comprises a layer of clear liquid from which most of the solids have settled out. Below this is an intermediate layer containing suspended solid particles which is generally referred to as the settling zone. The interface between the clear solution and the settling zone may be referred to as the upper boundary or slime level. At the bottom of the unit is a layer of settled sludge. Such a system is a dynamic one characterized by the movement of liquid and solid particles between the above zones. The levels of the three zones may vary considerably, depending upon the feed stream, operating conditions and other variables. To achieve maximum capacity with such a settling unit, it has generally been thought that the upper boundary should be maintained as close to the top of the unit as possible and that only a relatively thin layer of clarified solution be maintained above the floc layer.

It is conventional to add flocculants or coagulants to thickeners, decanters, clarifiers and similar settling devices to increase their capacity. These materials cause the suspended particles in the slurry or pulp to flocculate or agglomerate and thus settle more rapidly. The amount of flocculant or the like which is required at any particular moment depends in part upon the slurry or pulp feed rate, the solids content of the feed, the solids size range and distribution, the densities of the solid particles, and the temperature and other operating conditions. Under constant conditions, the amount of flocculant needed to achieve maximum capacity in a particular gravity settling unit is generally determined by trial and error. However, in actual practice the conditions may change due to variations in the amount and compositions of the solid suspended in the feed stream and other variables over which the operator of the unit may have relatively little or no control. Adjustments of the amount of flocculant added to the system is therefore necessary to compensate for the variations and maintain the desired capacity and degree of separation while at the same time keeping operating costs within acceptable bounds by eliminating overflocculation, and its related problems in downstream operations such as in the final polishing filtration.

It has been common practice to use the upper boundary of the settling zone within a settler as a measure of the settler's performance and to monitor this level as a means for determining the need for changes in the flocculant rate. In general, the higher the upper boundary, the more flocculant that is needed. This location of the upper boundary has generally been done manually by means of measuring sticks lowered into the vessel near the outer edge of the unit. Vacuum tubes, depth samplers, ultrasonic probes may also be used. The upper boundary is, however, not a direct measure of the settling characteristics of solids in the pulp or slurry and instead is the result of the combination of variables, including flocculant type and flow rate, solids feed rate, solids and liquid characteristics, mixing etc. There is normally a long time lag between the changes in the rate of addition of flocculant and corresponding changes in the upper boundary and hence the operator must estimate the amount of change in the rate of addition of flocculant which will be needed to produce a desired change in upper boundary. If he overestimates or underestimates the change in rate required, the unit may become unstable and eventually have to be shut down to avoid overloading or the carryover of solids. The upper boundary therefore provides at best a visible means for assessing the state of the thickener or clarifier operation and, if it increases progressively, it may serve as an delayed warning that the capacity of the settler has been exceeded.

Attempts have also been made to control the operation of a settler by sampling the incoming feed slurry to the feedwell at regular intervals downstream of the point at which flocculant is added to the feed slurry. The samples thus collected are passed to a laboratory sized gravity separation vessel where representative settling can take place. By sensing the interface level between the liquid and solid phases in the separation vessel and adjusting the rate of flocculant addition to the feed stream in accordance with variations in the level of the interface during operation of the system, it was hoped that the rate of addition of flocculant could be controlled automatically and that the flocculant consumption could be thereby substantially reduced. However, attempts to develop such a system in the past were abandoned because none was capable of providing reliable data necessary for the control and operation of a full size commercial settler.

One example of sampling equipment for measuring sedimentation rate is that described in Parker et al U.S. Pat. No. 4,318,296, issued Mar. 9, 1982. This system includes a sampling chamber for a sample to be tested, Elmer means for controlling a control means to stop the feed of suspension to the sampling chamber and means for retaining the height of the sample at a preselected level in the sampling chamber during a settling period. It also includes detector means for detecting when a boundary level defined by the settling solids in the sample in the sampling chamber reaches a further preselected level. The timer means determines the period of time elapsing between the stare of the settling period when the height of the sample is at the preselected level and the time when the detector means detects that the boundary level has reached the further preselected level.

Another control system is described in Valheim, "Flocculant Optimization Cuts Chemical Costs and Boosts Performance"; Process Control in Engineering; August 1990, pp. 34–35. That system measures continuously the concentration of suspended solids in the total flow of incoming slurry, the flow raze of the slurry and the turbidity of the material leaving the full size industrial settling unit. The turbidity is the control parameter for the flocculant dosage system.

In Eisenlauer et al "Z. Wasser Abwasser Forsch." 16, (1983) pp. 9–15 there is described a process for the control of flocculant to a settler which involves adding a varying amount of flocculant to a side stream of the suspension to be treated, and passing this mixture through a flow-through cell where the particle size distribution of the flocs is measured by a laser light scattering. This information determines the concentration at which flocculation begins, and the size and strength of the flocs.

Other control attempts have been made directly to full size settling devices such as that described in Chandler, U.S. Pat. No. 4,040,954, issued Aug. 9, 1977. This describes a process for controlling the settling rate by measuring continuously the turbidity of the suspension at a selected height in the full size settling vessel. The position corresponds to the upper limit of cloudy liquor or floc layer above the bottom layer of mud in a state of hindered settlement. This is done by measuring the light transmittance through a continuous sample withdrawn from the settling vessel, using a light beam from a light source directed through a curtain of liquor. When the turbidity is higher than the desired set point, indicating that the interface is going higher, the amount of flocculant is increased.

It is the object of the present invention to provide an improved testing system for measuring the settling characteristics of slurries and flocculant samples and using the results to either control a full size continuous industrial gravity settler or to construct such a full size settler.

SUMMARY OF THE INVENTION

One embodiment of the present invention relates to a testing device for use in determining optimum operating conditions for a full size industrial continuous gravity settling unit and for the design of such settling unit. The sample testing device comprises an elongated, cylindrical settling column having concentric, inner and outer transparent cylindrical walls forming an annular space therebetween filled with transparent heat exchange liquid, with the inner wall defining a cylindrical settling cell. A cylindrical feedwell extends downwardly into the top end of the settling cell and an overflow outlet opening is provided in the wall of the settling cell at a location above the bottom end of the feedwell. A solids discharge opening is provided at the bottom of the settling cell and a rotating rake is provided at the bottom of the settling cell to assist in compacting collected solids. Pump means are provided adapted to deliver smooth continuous flows of slurry and flocculant into the settler and mixing means are provided for mixing together the slurry and the flocculant. Also included are means for measuring and controlling the various flow rates and temperatures.

The device preferably includes separate reservoirs for the slurry to be tested and the flocculant to be tested. The slurry reservoir includes a mixer for mixing the slurry and heating means for maintaining the slurry at a uniform temperature. To assist in maintaining this uniform temperature, the slurry reservoir preferably has insulated walls and electric heating bands surrounding the sidewalls of the reservoir.

It is important that there be provided a smooth constant flow of slurry and flocculant to the feedwell. In order to achieve this, it is preferable to utilize a peristaltic pump for the feed slurry, and particularly a dual head, single drive peristaltic pump. It is also preferable to utilize a similar dual head, single drive peristaltic pump for adding the flocculant to the slurry at one or a plurality of addition points.

The slurry feed and flocculant are mixed in line before arriving at the feedwell of the column and the mixing is preferably aided by the use of at least one in-line static or rotary mixer. For instance, one mixer may be installed in the slurry feedline immediately downstream from the slurry feed pump and a second in-line mixer may be installed immediately before the feedwell. Other, additional points may also be used. The flocculant may be added to the slurry feedline before the first in-line mixer or before the second in-line mixer or at both locations.

The testing device of this invention simulates a full scale industrial continuous gravity settling unit in that it operates on a continuous basis with a continuous supply of feed slurry and of flocculant and a continuous withdrawal of settled solids and clarified liquor.

Because the walls of the sample settling column are transparent, the position and shape of the stream of agglomerated solids leaving the bottom of the feedwell of the settling cell can be observed and evaluated. The flow rate of the solution of flocculating agent is adjusted for a selected flow rate of the slurry stream of suspended solids to the settling vessel, so that the stream of agglomerated solids leaving the feedwell display what is known as "hindered" settling. The test can be repeated for other flow rates of the slurry stream of suspended solids. Hindered settling is a steady state settling in which the flocs are forced to take a direct path to the bottom of the settling vessel due to the high population of dense flocs in the surroundings.

When the slurry has been overflocculated because of an overdose of flocculant, the flocs are free to settle without any interaction from each other. This is generally known as "free settling".

When free settling is observed, as the dose of flocculant is decreased a modification of the morphology of the flocs can be observed. Thus, as the amount of flocculant dose is decreased, the flocs appear smaller in diameter, more compacted and they settle at a somewhat slower rate. When the state is reached where the flocculated particles are all about the same size and are distributed uniformly in the settling zone included between the outlet of the feedwell and the interface of the mud bed, the desired settling state known as "hindered" settling has been reached. At this point the flocculated particles interact frequently with each other and with the sidewalls of the cell such that the free path is at its smallest value. If at this point the flocculant dose is further reduced, the floc size is markedly reduced and solids start ascending above the feedwell and out in the overflow, indicating that the flocculant dose is too low.

When the state of "hindered" settling has been achieved and maintained at an equilibrium state for a period of at least 15 minutes, the optimum settling has been achieved for the particular conditions of flow rate of suspended solids, temperature etc. The flow rates, temperatures, flocculant concentration, slurry solid content, etc. are recorded for this equilibrium state of hindered settling and these recorded results are then used for calculations to either control and modify the addition of flocculant in the operation of a full size industrial continuous gravity settler or to provide the parameters needed to design a full size settler, such as liquid and solid fluxes, flocculant type and concentration and flow rate, temperature, solids in the underflow, clarity of the overflow etc.

The present invention is a device and process which permits the continuous observation of the flocculation and settling behaviour of a flowing slurry as a function of the concentration and flow rate of the flocculant. The observation can be done instantaneously by eye, or can be recorded on video tape or photographic film for evaluation at a later time. From these observations can be deduced:—the optimum dose of flocculant for a given flow of slurry to an industrial gravity settling device, and thus provide for the determination of the amount of flocculant to be added to give efficient operation;—the flux of solids and liquids, that is the capacity of the settler; and—the characteristics of the overflow and underflow; and furthermore provide information for the design and construction of an industrial size gravity settling device.

An example of how the observations are made on the behaviour of the settling slurry is shown in Table 1 below:

TABLE 1

|  | CONDITION I | CONDITION II | CONDITION III |
|---|---|---|---|
| Appearance of Overflow | Clear | Turbid | Clear |
| Appearance of Flocs | Predominantly Large | Predominantly Small | Uniformly of Intermediate Size |
| Behaviour of Flocs | Free Settling | Do not settle | Hindered settling |
| Conclusion Re Flocculant Dosage | Too much | Too little | Correct |

DESCRIPTION OF THE PREFERRED EMBODIMENTS

Summary of the Drawings

In the drawings which illustrate certain preferred embodiments of the present invention.

Figure 1:
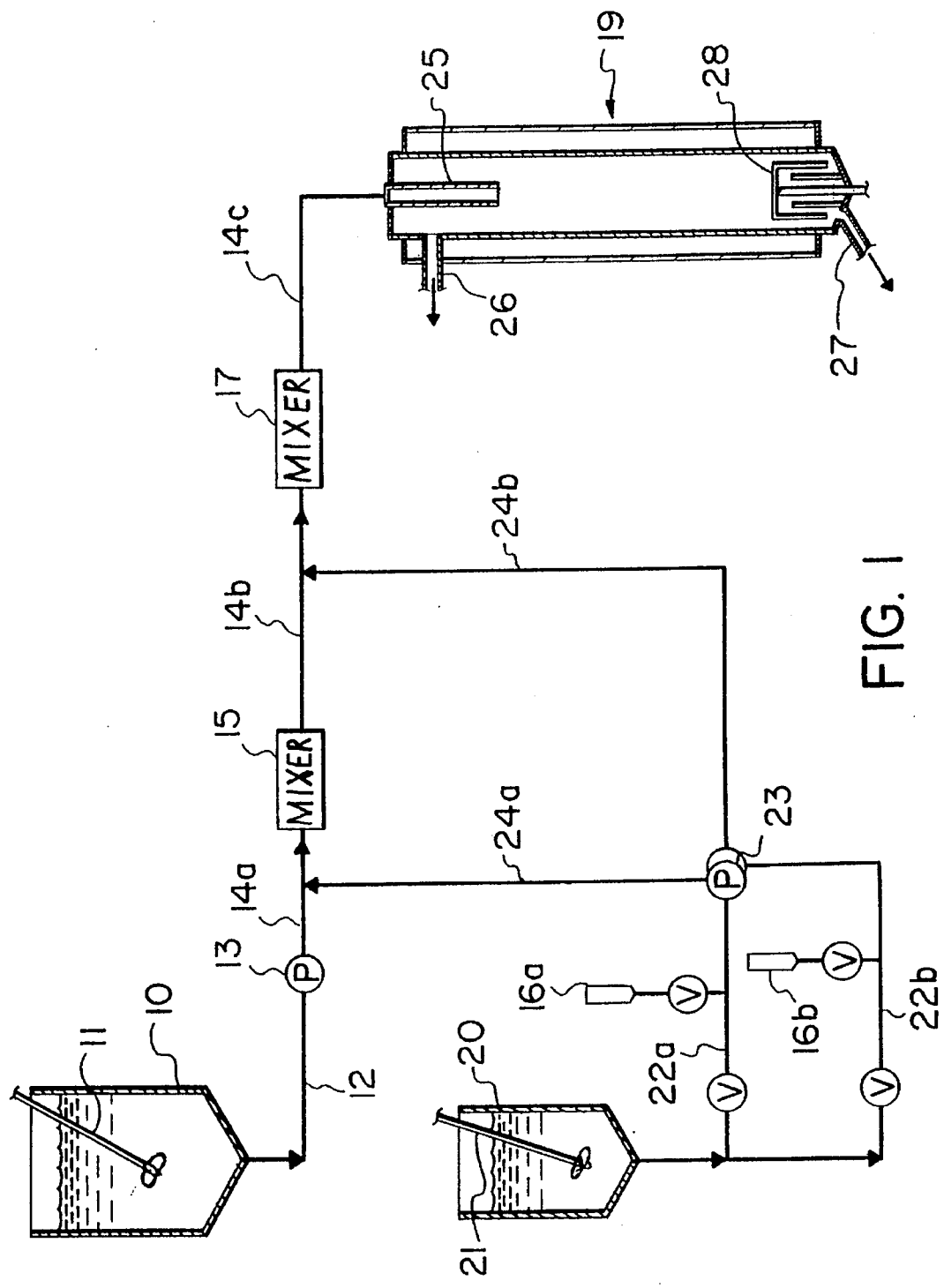
FIG. 1 is a schematic flow sheet of the testing device of the invention.

Turning now to the flow sheet of FIG. 1, the basic elements of the testing system of the invention include a slurry sample reservoir 10 with a mixer 11, a feed line 12 from the reservoir 10 to a dual head, single drive peristaltic pump 13. The outlet from pump 13 is pumped through the feed line 14a, 14b, 14c, containing in-line rotary or static mixers 15 and 17. The slurry feed is fed into feedwell 25 of settling column 19.

The flocculant is also held in a separate reservoir 20. A flocculant is fed via lines 22(a) and 22(b) to a second dual head, single drive peristaltic pump 23 and the outlet from pump 23 may be directed via line 24a to join line 14a immediately before mixer 15 or by line 24b into line 14b immediately before in-line mixer 17. If desired, the flocculant solution may be fed simultaneously through both of lines 24a and 24b. Draw-down tubes 16a and 16b are provided to calibrate the flow rates of the flocculant solution.

In the settling column 19, the overflow is drawn off through outlet 26 while the solids are moved through outlet 27, having been compacted by rakes 28.

Figure 2:
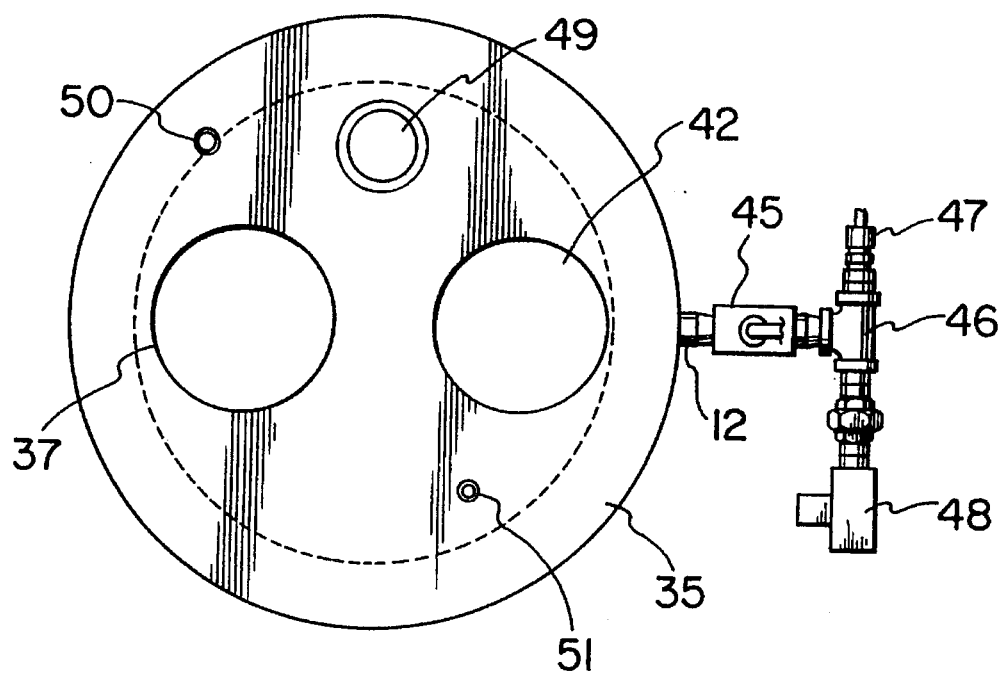
FIG. 2 is a plan view of a feed slurry reservoir.
Figure 3:
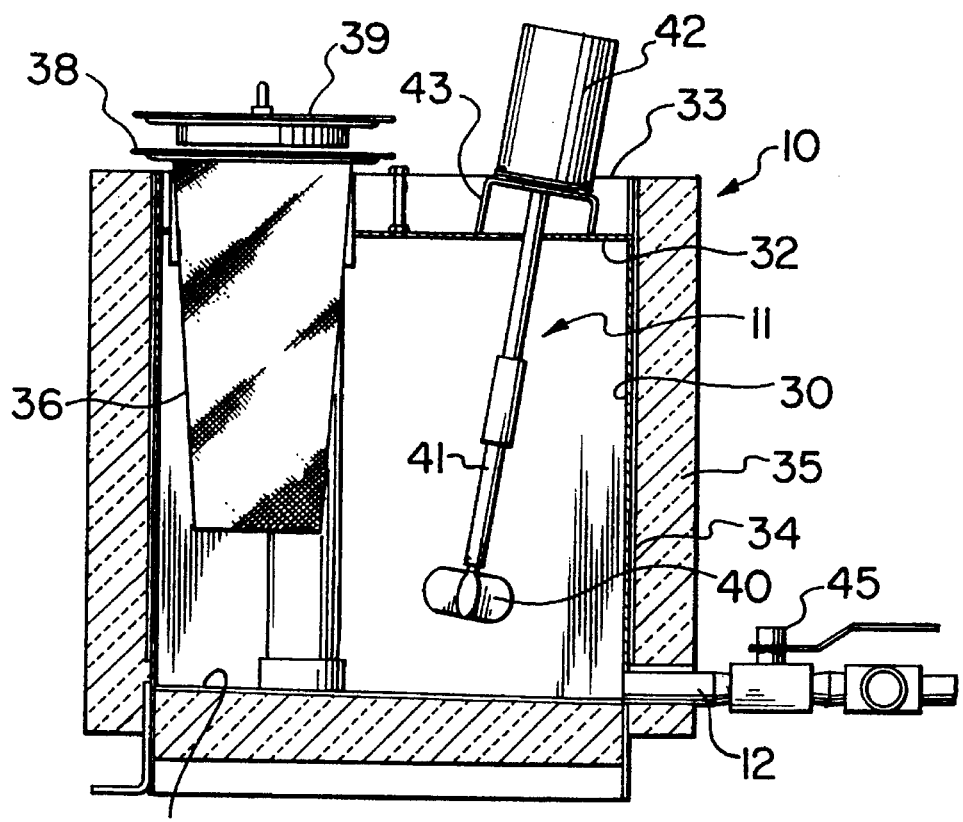
FIG. 3 is an elevation in partial section of the feed slurry reservoir.

The slurry sample reservoir 10 is described in greater detail in FIGS. 2 and 3. It comprises side walls 30, a bottom wall 31 and spaced top walls 32 and 33. The walls are insulated by glass fibre insulation 35 and the vessel is heated by means of electric heating bands 34 surrounding the sidewalls.

The slurry samples are fed into the reservoir 10 through an inlet mesh basket 36 which screens out oversized particles. The mesh basket 36, which fits into a hole 37 in the top 32, 33 of the reservoir, includes an upper flange 38 and a cover 39.

The slurry in the reservoir is maintained at a desired constant temperature and is thoroughly mixed by means of mixer 11 which includes mixing blades 40, a drive shaft 41, motor 42 and a motor mount 43.

The mixed and heated slurry is discharged through outlet 12 and then through valve 45 and T-member 46 and is either fed to pump 13 through connector 47 or sent to waste through valve 48.

Figure 4:
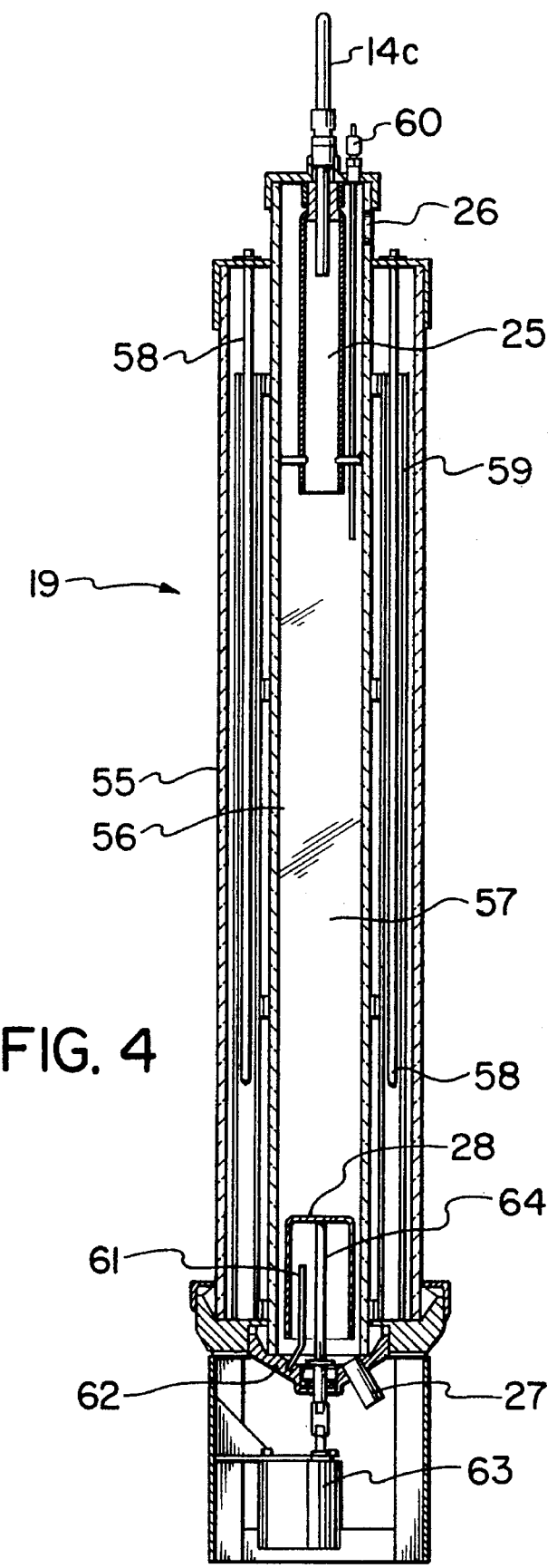
FIG. 4 is an elevation in partial section of the settling column.

The settling column is shown in some detail in FIG. 4 and it includes outer and inner cylindrical walls formed of clear acrylic tubes 55 and 56 forming an annular gap therebetween. This annular gap is filled by a transparent heat exchange fluid and is heated by means of heating rods 58 extending downwardly from the top. A thermocouple 60 is also included for determining the temperature of the settling zone 57.

As described earlier, the settling cell 57 includes a feedwell 25 extending downwardly into the top end thereof, an overflow 26, a bottom discharge 27 and a rake mechanism 28. The rake mechanism is mounted on a rotatable shaft 64 driven by motor 63 and the rake mechanism cooperates with fixed prongs 61 mounted in the bottom 62 of the settling cell.

Figure 5:
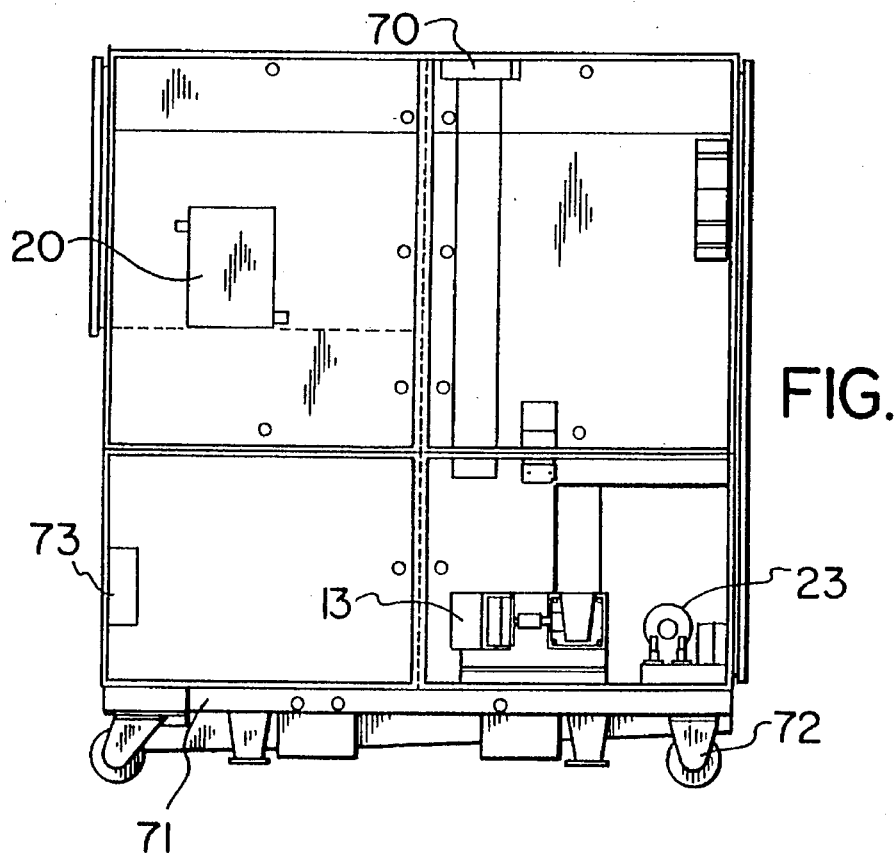
FIG. 5 is a rear elevation of a portable testing device.
Figure 6:
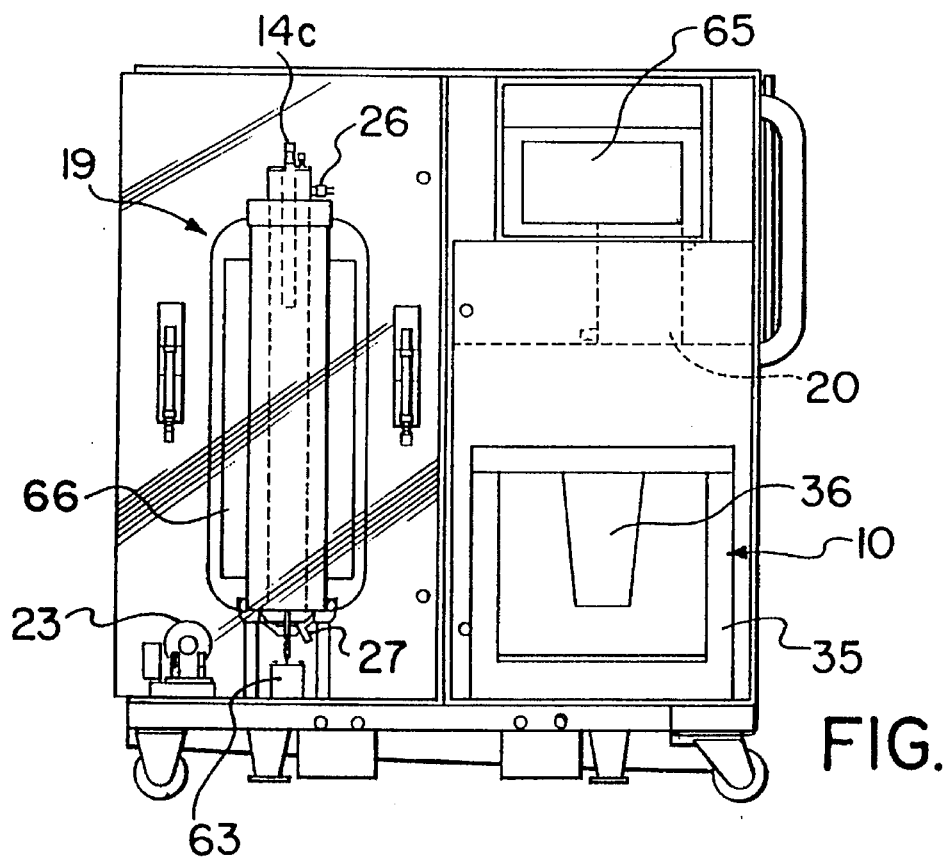
FIG. 6 is a front elevation of the device shown in FIG. 5.

A portable configuration of the sample testing device of the invention is shown in FIGS. 5 and 6 and this includes a bottom frame 71 supported on casters 72 for easy transportation. It is constructed with a rigid frame and the vertical walls are formed as either openable doors or removable panels for easy access to the interior of the unit. FIGS. 5 and 6 show the relative positions of the reservoirs 10 and 20 and the peristaltic pumps 13 and 23. The settling column 19 is placed inside a window for easy viewing and is preferably lighted by fluorescent lights 66 to improve visibility for observing the settling action. The system is completely operated by way of a control panel 65, which includes a PLC, "Programmable Logic Controller" and a Man/Machine interface (MMI) including a touch screen. The PLC and the MMI includes controls, interlocks and alarms to protect the operator and maintain the integrity and safety of the device.

The control system operates, controls, and records the operating data of the following: pumps, temperature probes, and safety interlocks. These provide the ease of operation, safety and ruggedness required for use in an industrial environment.

The data recording comprises noting the flow rate of the flocculant and the flow rate of the slurry at the time the desired flocculation and settling behaviour has been obtained and maintained for some time. These flow rates are derived from the direct reading of the rpm's of the pumps through calibration curves, which are checked regularly by the use of the draw down tubes for the flocculant, or the drop test of the reservoir for the slurry. From these flow rates and a knowledge of the dimensions of the apparatus, i.e. the area of the settler and the concentrations of flocculant in the flocculant solution and the amounts of solids is observed.

Further preferred embodiments of this invention are illustrated by the following examples.

EXAMPLE 1

This example demonstrates how the testing device of the invention is used to verify a process for the settling of a slurry of red muds, which is the residue or tailings of bauxite remaining after the extraction of alumina by the Bayer process.

The test sample contained a mixture of three different bauxites, comprising 65% Trombetas, 25% Boke and 10% Sierra Leone bauxite which had been processed. The resulting slurry of red mud had settled unsatisfactorily in the above industrial full size settler. This industrial settler normally gave a moderately clear overflow, containing 150 to 250 mg/l of suspended solids, a thick underflow containing 450–550 g/l of solids at a flux of solids of 9.6 Tonnes/(m$^2$.day) in a volumetric (liquid) flux of 14.3 m$^3$/(m$^2$.h) of incoming slurry.

The effects of using different flocculants and feed rates of red mud slurry were compared. Two different flocculants were tested, namely HX-200, a poly-hydroxamate supplied by Cytec Corporation and N9779, a poly-sodium acrylate supplied by Nalco Chemical Corporation. The flocculants were dissolved and diluted in a 10 g NaOH/L solution to a concentration of 0.04% w/w. The concentration of red mud solids in the slurry was kept at 26 g/l and the feed rates were varied.

The results of the tests are summarized in Table 2 and are compared with the usual operating results obtained with the industrial size settler, shown in the last column. These results show that both flocculants gave similar performance and that the clarity of the overflow at 300 mg/l and higher of suspended solids was unacceptable. Moreover, Nalco N9779 displayed poor overflow clarity at high feed rates. The fluxes of solids and of liquid are lower under all conditions than those normally encountered with the industrial settler and the amount of flocculant required is higher than that normally required. The conclusion from these observations is that the settler and the flocculants are providing the expected performance, and that the poor settling is caused by the particular mixture of bauxites in the feed. As a consequence, the proportions of the various bauxites was changed, to reduce the concentration of Sierra Leone bauxite and to increase the concentration of Trombetas bauxite. The new revised mixture provided satisfactory settling in the industrial settler.

EXAMPLE 2

This example shows how the testing device of the invention may be used to design a process and full size industrial equipment for settling of a slurry of red muds remaining after the extraction of alumina from a mixture of 65% Trombetas, 25% Boke and 10% Sierra Leone bauxite.

The procedure followed was similar to that shown in Example 1 and the flocculant used was a Nalco N9779 flocculant at a concentration of 0.04% w/w. This was tested by being added at one addition point as well as the two different addition points shown in FIG. 1 using rotary in-line mixers, and the results are summarized in Table 3. These results show that there was no difference between the one or two point addition in the flux of solids or liquids, i.e. the capacity of the decanter. However, the underflow contained more solids when the dosage of flocculant is increased. This higher concentration of solids is obtained through a two-fold increase in flocculant consumption, expressed as g/Tonne of solids and accompanied by a deterioration in the clarity of the overflow, expressed as a concentration of suspended solids. These results allow the design of a full size commercial settler, from the determined values of the flux of solids and the flux of liquid obtained at the optimum flocculant dosage.

EXAMPLE 3

This example demonstrates how the testing device of the invention may be used to design equipment for the separation of a different system, in this case a suspension of 52–106 g/l of precipitated alumina hydrate in Bayer process spent liquor, containing nominally 180 g/l of caustic expressed as $Na_2CO_3$ and 65 g/l of dissolved $Al_2O_3$. The settling behaviour of this slurry was studied as a function of feed rates of slurry, concentration of solids in the slurry feed, and addition of Alcar H4, a modified dextran flocculant supplied by Allied Colloids.

The results of this test are shown in Table 4. They show that (1) feed diluted to 52 g/L is not satisfactory, because this gives a poor clarity in the overflow of 860–1050 mg/L, lower flux of solids and liquid, i.e. lower efficiency, and requires higher dosages of flocculant; and (2) feed at 106 g/L is preferred because this gives the best clarity in the overflow, higher flux of solids and liquids, and requires a smaller dose of flocculant. They indicate that the highest flux of solids, at 21.7 Tonnes/m$^2$/day are obtained with a slurry containing 106 g/l of solids, which gives a liquid flux of 8.5 ma/(m$^2$.hour). This corresponds to an upward flow of liquor at 9.3 m/hour. This upward flow rate is acceptable, as is the consumption of flocculant at 43 g/Tonne of solids. The dimensions of the industrial sized settler are based directly on the fluxes derived from the sample testing settler results.

EXAMPLE 4

This demonstrates the use of the testing device of the invention to design equipment for settling of copper tailings. These tailings comprised quartz as a major constituent, along with kaolinite and muscovite as minor constituents. The tailings were suspended in water at a concentration between 72 and 408 g/L and the settling behaviour was studied as a function of concentration of solids in the slurry, feed rate and the addition of a 0.04% w/w solution of polyacrylamide flocculant at different dosage rates.

The results are shown in Table 5 and these indicate that the highest flux of solids at 59 Tonnes/(m$^2$.day) is obtained with a feed containing 400 g/l of solids, which requires the lowest flocculant addition of 19 g/Tonne of solids.

EXAMPLE 5

This example shows how the testing device of the invention may be used to design equipment for the settling of a suspension of red mud from the first stage of a countercurrent washing circuit to recover the caustic from the suspended red mud. This suspension contained between 100–150 g/L of solids in a solution containing 145 g/L of caustic expressed as $Na_2CO_3$, 25 g/L of sodium carbonate, 47 g/L of dissolved $Al_2O_3$. The settling behaviour was studied as a function of concentration of solids in the slurry, the feed rate of the slurry and the addition of 0.04% w/w solution of a N9779 flocculant supplied by Nalco Corporation at different dosage rates.

The results are shown in Table 6 and these indicate that the maximum throughput is 26.9 Tonnes/($m^2$·day) of solids at an upward flow velocity of 8.4 m/hour accompanied by acceptable overflow clarity, when the feed rate contains 145 g/l of solids, using 55 g/Tonne of flocculant.

Although the invention has been discussed above primarily in terms of the treatment of metallurgical pulps and similar slurries, it should be recognized that it is not limited to such applications and can also be utilized in sewage disposal plants, chemical plants, and a variety of other facilities requiring the use of thickeners and a similar continuous gravity sedimentation devices for the separation of a liquid suspension of solid particles into clarified liquid and sludge phases.

TABLE 2

| | Test | | | | Typical Industrial Settler |
|---|---|---|---|---|---|
| | 1 | 2 | 3 | 4 | |
| FLOCCULANT | | | | | |
| Type | Cytec HX-200 | | NALCO N9779 | | |
| Feed Rate | 1.1 | 5.4 | 1.5 | 6.0 | |
| Slurry Feed Rate mL/Min | 325 | 780 | 330 | 800 | |
| Conc'n of Solids g/L | 26 | 26 | 26 | 26 | |
| RESULTS | | | | | |
| Upward Flow m/h | 5.5 | 13.2 | 5.6 | 13.5 | 14.3 |
| Overflow Solids mg/L | 325 | 310 | 346 | 740 | 150–250 |
| Underflow Solids g/L | 513 | 289 | 380 | 421 | 450–550 |
| Flux of Solids T/($m^2$·Day) | 3.2 | 7.6 | 3.2 | 7.8 | 9.6 |
| Flux of Liquid $m^3$/($m^2$·h) | 5.1 | 12.2 | 5.1 | 12.5 | 14.3 |
| Flocculant g/T | 52 | 107 | 70 | 115 | 46 |

TABLE 3

| | Test | | | |
|---|---|---|---|---|
| | 1 | 2 | 3 | 4 |
| FLOCCULANT | | | | |
| Feed Rate mL/min | 2.7 | 4.2 | 2.5 | 4.1 |
| CONDITIONS | | | | |
| Number of Addition Points | 1 | 1 | 2 | 2 |
| Slurry Feed Rate mL/Min | 310 | 295 | 300 | 300 |
| Conc'n of Solids g/L | 25 | 25 | 25 | 25 |
| RESULTS | | | | |
| Upward Flow m/h | 5.2 | 5.0 | 5.1 | 5.1 |
| Overflow Solids mg/L | 516 | 489 | 429 | 604 |
| Underflow Solids g/L | 161 | 258 | 132 | 215 |
| Flux of Solids T/($m^2$·Day) | 2.9 | 2.8 | 2.8 | 2.8 |
| Flux of Liquid $m^3$/($m^2$·h) | 4.8 | 4.6 | 4.7 | 4.7 |
| Flocculant g/T | 139 | 228 | 133 | 219 |

TABLE 4

| | Test | | | |
|---|---|---|---|---|
| | 1 | 2 | 3 | 4 |
| FLOCCULANT | | | | |
| Feed Rate mL/min | 2.0 | 0.6 | 1.5 | 3.5 |
| CONDITIONS | | | | |
| Slurry Feed Rate mL/Min | 548 | 140 | 300 | 600 |
| Conc'n of Solids g/L | 106 | 106 | 52 | 52 |
| RESULTS | | | | |
| Upward Flow m/h | 9.3 | 2.4 | 5.1 | 10.1 |
| Overflow Solids mg/L | 230 | 350 | 860 | 1050 |
| Underflow Solids g/L | 323 | 456 | 560 | 467 |
| Flux of Solids T/($m^2$·Day) | 21.7 | 5.6 | 5.8 | 11.7 |
| Flux of Liquid $m^3$/($m^2$·h) | 8.5 | 2.2 | 4.7 | 9.4 |
| Flocculant g/T | 43 | 51 | 120 | 140 |

TABLE 5

| | Test | | | |
|---|---|---|---|---|
| | A | B | 1 | 2 |
| FLOCCULANT | | | | |
| Feed Rate mL/min | 2.8 | 3.5 | 11.5 | 5.4 |
| CONDITIONS | | | | |
| Slurry Feed Rate mL/Min | 380 | 800 | 333 | 333 |
| Conc'n of Solids g/L | 102 | 72 | 230 | 408 |
| RESULTS | | | | |
| Upward Flow m/h | 7.6 | 15.9 | 6.0 | 6.6 |
| Flux of Solids T/($m^2$·Day) | 16.8 | 25.0 | 33.3 | 59.0 |
| Flux of Liquid $m^3$/($m^2$·h) | 5.7 | 12.0 | 5.0 | 5.0 |
| Flocculant g/T | 34 | 29 | 71 | 19 |

TABLE 6

| | Test | | | | |
|---|---|---|---|---|---|
| | 1 | 2 | 3 | 4 | 5 |
| FLOCCULANT | | | | | |
| Feed Rate mL/min | 5.5 | 9.9 | 3.9 | 6.0 | 10.0 |
| CONDITIONS | | | | | |
| Slurry Feed Rate mL/Min | 270 | 495 | 270 | 505 | 750 |
| Conc'n of Solids g/L | 145 | 145 | 100 | 100 | 100 |
| RESULTS | | | | | |
| Upward Flow m/h | 4.6 | 8.4 | 4.6 | 8.5 | 12.7 |
| Overflow Solids mg/L | 130 | 164 | 159 | 115 | 236 |
| Underflow Solids g/L | 310 | 215 | 311 | 213 | 250 |
| Flux of Solids T/($m^2$·Day) | 14.6 | 26.9 | 10.1 | 18.9 | 28.1 |
| Flocculant g/T | 56 | 55 | 58 | 48 | 53 |

We claim:

1. A testing device for use in determining optimum operating conditions for a full size industrial continuous gravity settling unit and for the design of such settling unit; said testing device comprising:

an elongated, vertical, cylindrical settling unit having concentric, inner and outer transparent cylindrical walls forming an annular space therebetween filled with transparent heat exchange liquid and said inner wall defining a cylindrical settling unit, a cylindrical feedwell extending downwardly into the top end of the settling unit, an overflow outlet opening in said inner wall at a location above the bottom end of said feedwell, a solids discharge opening at the bottom of said settling unit and a rotating rake at the bottom of the settling zone for compacting collected solids, pump means for providing smooth, continuous flows of slurry and flocculant, mixing means for mixing together said slurry and said flocculant, and means for measuring and controlling flow rates and temperatures.

2. A device according to claim 1, which includes a reservoir for slurry to be tested and a reservoir for flocculant to be tested.

3. A device according to claim 2 wherein the slurry reservoir includes a mixer for mixing the slurry and heating means for maintaining the slurry at a uniform temperature.

4. A device according to claim 3 wherein the slurry reservoir has insulated walls.

5. A device according to claim 3 wherein the slurry reservoir and the flocculant reservoir are flow connected to separate peristaltic pumps.

6. A device according to claim 5 wherein the peristaltic pumps are dual head, single drive peristaltic pumps.

7. A device according to claim 3 wherein the pump means are flow connected to a single feedline to the feedwell of said settling unit.

8. A device according to claim 7 wherein said feedline includes at least one in-line static or rotary mixer.

9. A device according to claim 3 wherein the rotatable rake at the bottom of the settling zone comprises a U-shaped member with downwardly directed prongs connected to a rotatable shaft.

10. A device according to claim 9 wherein the bottom of the settling zone also includes fixed, upwardly directed prongs adapted to cooperate with said downwardly directed prongs.

11. A device according to claim 1 which includes a programmable logic controller (PLC) and a man machine interface (MMI) for operating, controlling and recording data.

12. A method for determining the optimum operating conditions for a full size industrial continuous gravity settling unit utilizing a small scale sample setting vessel, comprising the steps of:

(a) sampling incoming streams of suspended solids and flocculating agent, (b) providing means for measuring and adjusting the flow rates of the sample streams, (c) continuously mixing said sample streams of suspended solids and flocculating agent and continuously introducing a mixed stream of suspended solids and flocculating agent into the feedwell of a small scale settling vessel, (d) observing the position and shape of a stream of agglomerated solids leaving the bottom of the feedwell of the settling unit and adjusting the flow rate of at least one of the flow rate of the stream of suspended solids and the flow rate of the stream of flocculating agent to the settling vessel such that the stream of agglomerated solids leaving the feedwell displays hindered settling, and (e) utilizing said adjusted flow rates of the suspended solids stream and the flocculant stream to determine the optimum operating conditions for said settling unit.

13. A method according to claim 12 wherein the the position and shape of said stream of agglomerated solids is observed visually.

14. A method according to claim 12 wherein the portion and shape of said stream of agglomerated solids is recorded on a tape or film.

15. A method according to claim 12, wherein a clear overflow stream is continuously discharged from said settling unit at a location above the bottom of the feedwell.

16. A method according to claim 15, wherein collected solids are continuously discharged from the bottom of said settling unit.

17. A method according to claim 16, wherein the sample streams are pumped by means of dual head, single drive peristaltic pumps and the pumped streams are mixed in at least one in-line static or rotary mixer.

18. A method according to claim 12, which includes calculating the flow rates of the suspended solids stream and flocculant stream for hindered settling in the small scale settling unit and correspondingly adjusting the suspended solids flow rate and the flocculant flow rate of the industrial settling unit.

19. The method for determining the optimum dimensional and a flow parameters in the design and construction of a full size industrial continuous gravity settling unit, comprising the steps of:

(a) obtaining samples of suspended solids to be settled and flocculant to be used in the settling, (b) pumping continuous streams of said samples, (c) providing means for measuring and adjusting the flow rates of the sample streams, (d) continuously mixing said sample streams of suspended solids and flocculating agent and continuously introducing a mixed stream of suspended solids and flocculating agent into the feedwell of a small scale settling unit, (e) observing the position and shape of a stream of agglomerated solids leaving the bottom of the feedwell of the settling unit and adjusting the flow rate of at least one of the flow rate of the stream of suspended solids and the flow rate of the stream of flocculating agent to the settling vessel such that the stream of agglomerated solids leaving the feedwell displays hindered settling, and (f) utilizing said adjusted flow rates of the suspended solids stream and the flocculant stream to determine the flux of solids, expressed as weight of solids per unit area of settling zone per day, and the flux of liquid, expressed as volume of liquid per unit area of settling zone per hour, and calculating therefrom the dimensions and optimum capacity for an industrial settling unit.

20. A method according to claim 19 wherein the position and shape of said stream of agglomerated solids is observed visually.

21. A method according to claim 19 wherein the portion and shade of said stream of agglomerated solids is recorded on a tape or film.

* * * * *